United States Patent [19]

Amano et al.

[11] 4,071,299

[45] Jan. 31, 1978

[54] TRANSMITTANCE DENSITOMETER

[75] Inventors: Tadashi Amano; Yoshitaka Mukaihara; Tadashi Nakamura, all of Hino, Japan

[73] Assignee: Konishiroku Photo Industry Co., Ltd., Tokyo, Japan

[21] Appl. No.: 686,268

[22] Filed: May 14, 1976

[30] Foreign Application Priority Data

May 16, 1975 Japan .................................. 50-65149

[51] Int. Cl.² ............................................ G01N 21/22
[52] U.S. Cl. .................................................. 356/202
[58] Field of Search ................................ 356/202, 201

[56] References Cited

U.S. PATENT DOCUMENTS

| 2,235,590 | 3/1941 | Rockwell | 356/202 |
| 2,567,005 | 9/1951 | Bennes | 356/202 |
| 3,375,751 | 4/1968 | Engborg et al. | 356/202 |

Primary Examiner—Paul A. Sacher
Assistant Examiner—R. A. Rosenberger
Attorney, Agent, or Firm—Martin A. Farber

[57] ABSTRACT

In a transmittance densitometer comprising a sample stage with a central measuring light path passing therethrough which is illuminated interiorly, there are provided a semi-transparent illumination plate provided for the sample stage, the semi-transparent illumination plate surrounding the measuring light path and capable of diffusing transmission light, and a local illumination chamber disposed beneath the illumination plate, the chamber optically isolated from illumination light directing to the measuring light path and the sample stage, whereby an illumination lamp disposed interiorly of the local illumination chamber is turned on under the control of the level of an ambient light shielding cylinder which partially defines the measuring light path.

11 Claims, 5 Drawing Figures

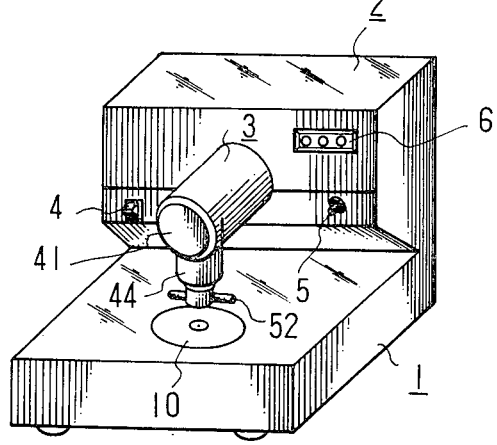
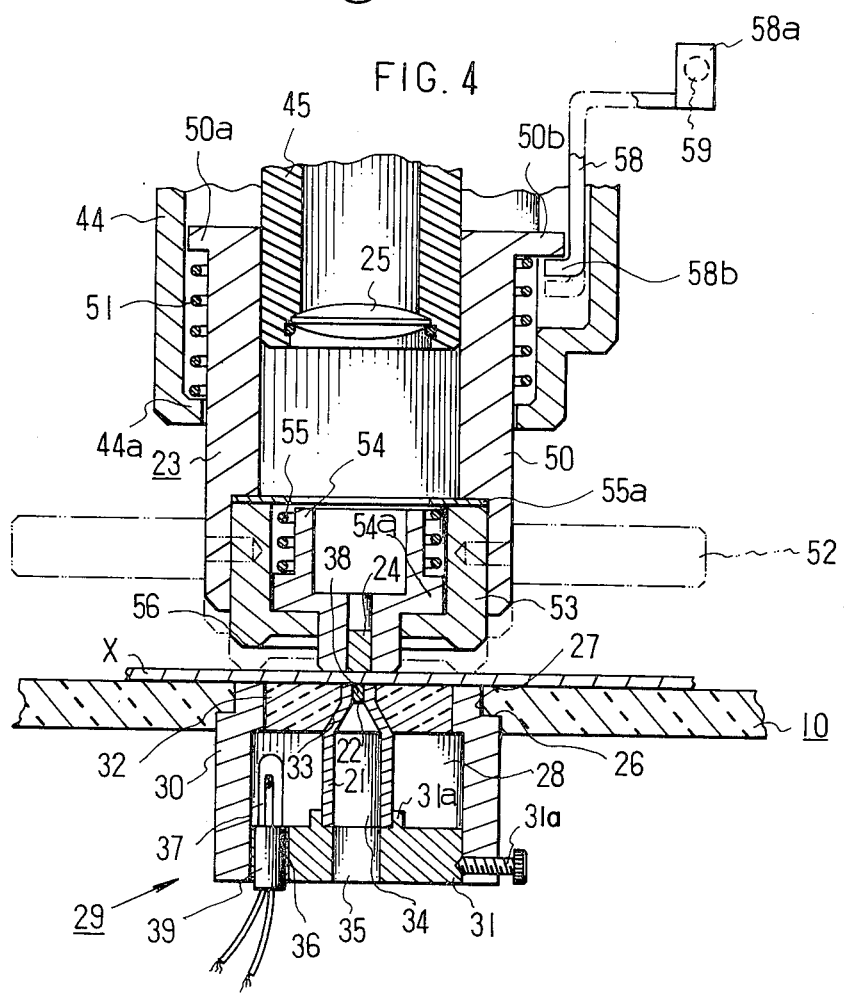

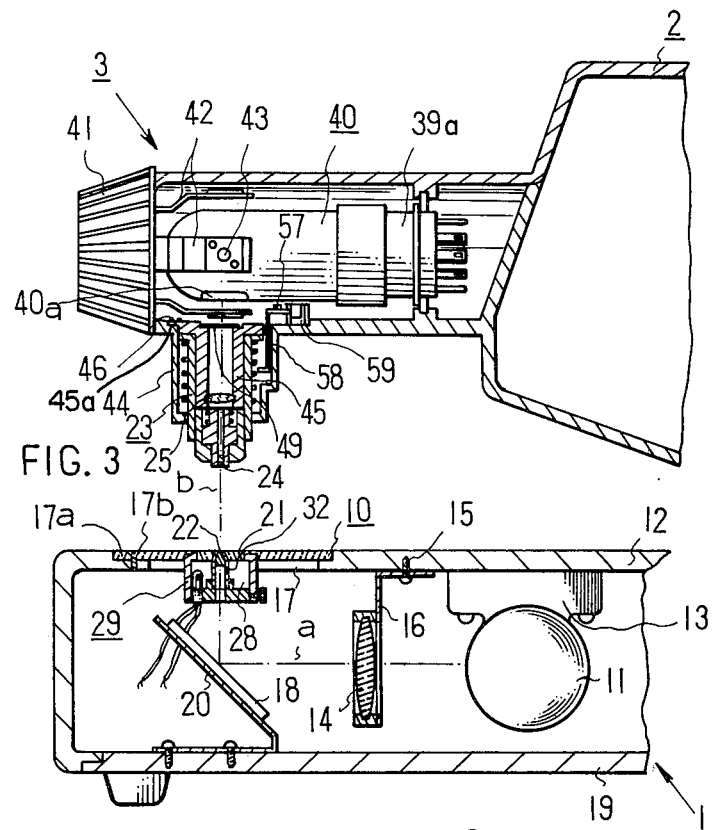

TRANSMITTANCE DENSITOMETER

FIELD OF THE INVENTION

This invention relates to a transmittance densitometer for use in measuring optical density of photographic pictures, and more particularly to a transmittance densitometer for measuring transmittance density of photographic films and the like.

BACKGROUND OF THE INVENTION

Generally, in a transmittance densitometer, the measuring area or the diameter of an aperture path is 0.5 mm (about 0.0197 inches), 1.0 mm (about 0.039 inches) or 2.0 mm (about 0.078 inches). When designing densitometers of this type, the size of the light receiving diffuser disposed on the measuring light path is selected to be larger than the diameter of a maximum aperture in consideration of reliable transmission of light from the aperture to the diffuser.

In order to be able to visually confirm what portion of a sample is measured, a sample stage is made from a semi-transparent light-diffusion plate and illuminated interiorly. With this sample stage illuminated interiorly, however, the light illuminating the sample stage impinges, upon the diffuser to give rise to degradation in measurement accuracy because the outer diameter of the diffuser is far larger than the diameter of the aperture. Therefore, in a conventional light transmission type densitometer, the sample stage is provided on its surface with an apertured opaque disc of about 10 mm (about 0.39 inches) diameter surrounding the measuring light path.

The apertured opaque disc, however, prevents the neighbourhood of the measuring location on a film from being illuminated, thereby giving rise to difficulties in visual confirmation of the measuring location. These difficulties are fatal when the optical density at the measuring location is approximately to that of its neighbourhood. Thus, an operator tends to perform measurement of an unintended portion of a sample.

SUMMARY OF THE INVENTION

A principal object of this invention is to provide a transmittance densitometer free from the above-mentioned defect.

Another object of the invention is to provide a transmittance densitometer which enables accurate measurement only of the intended portion of a sample.

According to this invention, the above object can be accomplished by providing a transmittance densitometer comprising a sample stage with a central measuring light path passing therethrough which is illuminated interiorly, and a vertically movable ambient light shielding cylinder disposed along the extension of the measuring light path and surrounding a light path communicated with the measuring light path, characterized in that the meter comprises an illumination plate of a semi-transparent substance disposed in the sample stage coaxially therewith to surround the measuring light path and capable of diffusing transmission light, an internal light shielding box constituting beneath the illumination plate a local illumination chamber optically isolated from illumination light directing to the measuring light path and the sample stage, an electric switch responsive to the level of the ambient light shielding cylinder, and an illumination lamp disposed in the local illumination chamber and being turned off by the electric switch when the ambient light cylinder is moved to be close to the sample stage. With this construction, this invention is advantageous in that the neighbourhood of the measuring location of a film picture is clearly illuminated to facilitate visual search of the measuring location, and that the illumination lamp is turned off automatically during measurement to eliminate an error caused by a light from the illumination lamp upon measured values.

While, in a preferred embodiment of this invention to be described later, the sample stage will be described in terms of an aperture stage formed with an aperture for restricting the diameter of light path, the sample stage may be altered to be incorporated with the light receiving diffuser. In such alternation, an aperture is formed at the lower end portion of the ambient light shielding cylinder, and measuring light is transmitted to the light receiving diffuser through the aperture. In another preferred embodiment of this invention, an annular edge projects from the end surface of the ambient light shielding cylinder, which annular edge may be brought into contact with the end surface of the internal light shielding box. The annular edge engages the end surface of the internal light shielding box to shield almost completely the measuring light path against ambient stray light and illumination light from the sample stage, thereby eliminating errors in measurement due to the ambient light. Further, the light receiving diffuser or the light transmitting aperture supported by or formed in a hollow member biased to project from the end surface of the ambient light shielding cylinder may improve accuracy of measured values, as will be seen from the following detailed description.

BRIEF DESCRIPTION OF THE DRAWINGS

Other objects and advantages of this invention will become clear from the following detailed description taken in conjunction with the accompanying drawings in which:

FIG. 1 is a perspective view generally depicting a transmittance densitometer;

FIG. 2 is a block diagram of a transmission system of the densitometer shown in FIG. 1;

FIG. 3 is a longitudinal sectional view of the densitometer depicting an overall measuring light path system;

FIG. 4 is a longitudinal sectional view, enlarged in part, depicting a positional relation between the ambient light shielding cylinder at the state immediately before measurement and the aperture stage; and FIG. 5 is a circuit diagram of one example of switching circuit for controlling the illumination lamp.

DETAILED DESCRIPTION OF THE PREFERRED EMBODIMENTS

Referring now to FIG. 1, there is shown a transmittance densitometer to which the present invention is applied, the densitometer being capable of digitally indicating color transmittance density and neutral transmittance density within 0.00 to 4.00 range. Obviously, the transmittance densitometer may readily be modified by the well-known technique into analog indication types or digital printing types. The transmittance densitometer generally comprises a measuring desk 1 having thereon a sample stage, a housing 2 installed on the rear portion of the measuring desk 1 for accommodating electric circuitries and a light receiving system casing 3 horizontally and forwardly extending from the housing 2. The housing 2 is provided with a power switch 4, a zero-adjust button 5 and a digital indicator (referred to as a digital indicator F with reference to FIG. 2) for indicating a measured density, these elements being arranged on the front panel of the housing 2.

As shown in FIG. 2, an input light signal from a diffuser described later is converted into an electric signal by a photoelectric convertor i.e., photomultiplier A, from which an output signal is supplied to a conversion circuit B for logarithmically converting the output of the photomultiplier A. The photomultiplier A and the conversion circuit B are supplied with a hold signal from a control circuit C. The hold signal is disabled by a trigger signal from a phototransistor to be described later.

The output of the conversion circuit B is delivered to a calibration circuit D for calibrating the output of the circuit B so that when the sample is not present on the stage, an indicator F indicates zero. An output signal of the calibration circuit D is converted into a digital signal at an A-D converter circuit E and then supplied to the aforesaid digital indicator F to be indicated as a digital form.

FIG. 3 shows in greater detail the interior of the measuring desk 1 and the light receiving system casing 3. Disposed interiorly of the measuring desk 1 is a main lamp 11 which is used as both measuring light source and internal illumination light source for the stage 10 to be detailed later. The main lamp 11 which is received in a socket mounted to the lower surface of a table 12 of the measuring desk 1 may be realized by, for example, an optical tungsten bulb having stable light quantity and color temperature. Within the illumination area of the main lamp 11 is disposed a condenser lens 14 which is preferably combined with a thermoproof filter. The condenser lens 14 is supported by an L-shaped bracket 16 secured to the lower surface of the table 12 with screws 15.

In the table 12 of the measuring desk 1 is formed a window 17 of a relatively large area, the window 17 having a large diametered section and a small diametered section adjacent thereto to leave a step 17a. Thus, in the large diametered section is seated the aperture stage 10 which is a diffusion plate made of a flat and smooth acrylic plate or a glass plate laminated with light scattering layers. The upper surface of the aperture stage 10 is flush with that of the table 12. It is preferable to prepare a plurality of sheets of the stage with different diameter apertures in order to allow the size of an incident light aperture, to be described later, to be changed in accordance with variety of measuring purposes. Accordingly, the aperture stage 10 is removably mounted to the table 12 by screws 17b to be screwed into the step 17a. The aperture stage 10 is illuminated interiorly by the light from the main lamp 11 which is directed to the window 17 so that a picture imaged on a sample of negative film placed on the measuring desk 1 can be observed.

The measuring desk 1 is interiorly incorporated with a reflection mirror 18 disposed right below the window 17, and the reflection mirror 18 is supported by a holder 20 fixed to a bottom plate 19 of the stage 10. The reflection mirror 18 mounted inclinedly 45° with respect to optical axis $a$ of the condenser lens 14 serves to reflect parallel light beams toward measuring light path $b$. The measuring light path $b$ is defined by an aperture 22 at the tip of a tube 21, a diffuser 24 at the lower end of an ambient light shielding cylinder 23 and a condenser lens 25. These members will be described later.

In register with the center of the aperture stage 10, on the other hand, is formed a circular hole 27 stepped at 26 as exaggerated in FIG. 4. In the circular hole 27, there is provided an internal light shielding box 29 which constitutes, interiorly of the measuring desk 1 and in cooperation with the tube 21, a local illumination chamber 28 optically isolated from the measuring light path and the aperture stage 10. Thus, the tube 21 is surrounded by the annular local illumination chamber 28 which in turn is surrounded by the internal light shielding box 29. The internal light shielding box 29 comprises a cylindrical wall 30 bonded to the stage 10 at the circular hole 27, a disc 31 fitted in the lower end of the cylindrical wall 30 and a stopper screw 31a screwed into a portion adjacent the lower end of the cylindrical wall 30. To the upper end inner surface of the cylindrical wall 30 is bonded by bonding agent an illumination plate 32 made of a material same as or similar to that of the stage 10. In a tapered central hole 33 of the illumination plate 32 is fitted the upper end of the tube 21. The disc 31 has at its center a circular hole 35 communicated with a hole 34 of the tube 21, and a lower end portion of the tube 21 is received by an annular extention 31a of the disc 31. The disc 31 is also formed with a hole 36 in which a socket 39 is held for receiving an illumination lamp 37 whose head lies in the local illumination chamber 28.

As has been explained herein before, the internal light shielding box 29 and the illumination plate 32 are so designed as to provide the local illumination chamber 28 optically isolated from the measuring light path and the stage 10. Consequently, it is possible to illuminate by light from the illumination lamp 37 the neighbourhood of a picture to be measured of a film X placed on the stage 10. It is also possible to replace the stage 10 with another stage having a different diameter aperture by removing the screw 31a.

Further, it is preferable to fill the aperture 22 of the tube 21 with a transparent substance 38. The transparent substance 38 is effective to prevent the aperture 22 from being chocked up by foreign substances such as dust so that it is possible to prevent the degradation in measurement accuracy due to wet films used or intrusion of dust.

Returning to FIG. 3, a socket 39a lying horizontally is fixed in the light receiving system casing 3. Carried by this socket 39a is a photomultiplier 40 (designated at A in FIG. 2) with its light receiving window 40a faced downward. A filter change knob 41 is rotatably mounted to the fore end of the light receiving system casing 3. The filter change knob 41 can be brought into a quasi-stationary state at every 90° interval. Where the meter is designed for a monochromatic film exclusive use type, the filter change knob 41 may be eliminated. Four filter support plates 42 arranged around the photomultiplier 40 are supported by the filter change knob 41 and they have an opening 43, in correspondence with the light receiving window 40a, to which an amber filter, red filter, green filter or blue filter is mounted.

Adjacent the fore end and at the lower side of the light receiving system casing 3, a hollow and vertically extending cylinder 44 integral with the casing is provided. Inside the cylinder 44, a guide cylinder 45 with an upper end flange 45a fixed to the light receiving system casing 3 by screws 46 (FIG. 3) is disposed coaxially with the cylinder 44. An ambient light shielding cylinder 23 which is vertically slidable along the guide cylinder 45 is provided in the extension cylinder 44. The condenser lens 25 disposed inside the guide cylinder 45 serves to focus incident light from the diffuser to be detailed later upon the light receiving window 40a. Preferably, an ND filter or auxiliary diffuser 49 is interposed between the condenser lens 25 and the light receiving window 40a. The ambient light shielding cylinder 23 comprises a shield 50 biased upward by a compressed spring 51 interposed between end wall 44a of the cylinder 44 and the flange 50a, a hollow head chip 53 housed by the lower end portion of the shield 50 and prevented from dropping by an operation handle 52 screwed into the shield 50, and a hollow member 54 slidable within the head chip 53 and provided with the diffuser 24 at its lower end. A washer 55a is received by the shield 50, and the hollow member 54 is biased downward by compressed spring 55 interposed between the washer 55a and a flange 54a of the hollow member 54. In this embodiment, an annular edge 56 is provided projecting from the bottom surface of the head chip 53, which annular projection may engage the top surface of the cylindrical wall 30. This annular edge 56, however, may be provided for the hollow member 54. Therefore, when the ambient light shielding cylinder 23 is depressed to a position designated at chained lines for measurement, the measuring light path b is shielded almost completely from ambient light by means of the internal light shielding box 29 and the ambient light shielding cylinder 23, thereby eliminating measuring errors due to ambient light.

On the other hand, a switch member 58 is suspended by a leaf spring 57 (FIG. 3) inside the light receiving system casing 3. The switch member 58 has shutter blade 58a on the both sides of which is disposed a photoelectric switch assembly which is schematically designated by a symbol 59. A light emission diode and a phototransistor opposed to each other, for example, stand for the photoelectric switch assembly 59. Lower hook 58b of the switch member 58 is associated with a paw 50b of the shield 50 within the movement range of the paw 50b. Consequently, when the ambient light shielding cylinder 23 is fully depressed up to the level designated at chained lines in FIG. 4, the phototransistor of the photoelectric switch assembly 59 operates.

FIG. 5 shows a control circuit for the illumination lamp 37 by way of an example. As diagrammatically shown therein, a switching transistor TR biased by the phototransistor PT which constitutes a part of the photoelectric switch assembly 59, has its collector connected to a relay coil L and a brake switch switched by the relay coil L is connected with the illumination lamp 37 in series. Consequently, when the switching transistor TR is enabled in response to the detection of light of the phototransistor PT, the relay coil L is excited to open the brake switch S, thereby turning off the illumination lamp 37. Thus, by utilizing a signal of the phototransistor TR as a trigger signal for disabling a hold signal transmitted from the control circuit C of FIG. 2, the photomultiplier A liable to be damaged by an excessive input signal can be protected from an accidental input signal. More particularly, when the operation handle 52 is lowered during measurement, the diffuser 24 first comes into contact with the film X as illustrated in FIG. 4 at solid lines thereby to prevent unwanted ambient stray light or light from the stage 10. At this level, however, since the paw 50b does not engage the lower hook 58b, the ambient light shielding cylinder 23 can be further lowered, compressing the compression spring, so that the annular edge 56 further shields by surrounding of the diffuser 24. As a result, the shutter blade 58a is lowered to enable the phototransistor TR, thereby preventing the photomultiplier A from being supplied with an excessive input signal.

Although the invention has been shown and described in terms of a preferred embodiment thereof, it will be understood that many changes and modifications may be made within the spirit and scope of the invention as defined in the appended claims.

What is claimed is:

1. In a transmittance densitometer comprising an annular sample stage with a central measuring light path passing centrally therethrough which is illuminated interiorly by illumination light, and a vertically movable ambient light shielding cylinder disposed above the sample stage and along the extension of the measuring light path and surrounding a light path communicating in extension with the measuring light path, the improvement which comprises
    an annular illumination plate made of a semi-transparent substance disposed centrally inside of said sample stage coaxially therewith annularly surrounding the measuring light path and capable of diffusing transmission light,
    an internal light shielding box defining a light shielding cylinder and disposed beneath said illumination plate forming a local illumination chamber optically isolated from the illumination light in the measuring light path and the sample stage,
    an electric switch means for responding to the level of the ambient light shielding cylinder relative to the sample stage, and
    an illumination lamp disposed in said local illumination chamber and operatively connected to said electric switch means for being turned off by said electric switch means when said ambient light shielding cylinder is moved so as to be close to said sample stage.

2. The densitometer according to claim 1, wherein said ambient light shielding cylinder includes a lower annular edge projection, the latter operatively engages an upper end surface of said internal light shielding box.

3. The densitometer according to claim 1, wherein said ambient light shielding cylinder comprises,
    a cylindrical shield,
    first means for normally biasing said shielding cylinder upwardly, the latter being forcibly depressible counter to said first biasing means, and
    a hollow member,
    second means for biasing said hollow member downwardly so as to project from said shield, and said hollow member is slidably disposed in said shield,
    said electric switch means being disposed at a level such that it is enabled only when said shield is depressed against a biasing force of said hollow member of said second biasing means.

4. The densitometer according to claim 3, further comprising
    an outermost vertically extending cylinder and an innermost guide cylinder coaxially spaced from each other and secured to each other at upper ends thereof defining an annular space therebetween, the latter opening at a bottom thereof, said outermost vertically extending cylinder is formed at the bottom with a radially inwardly directed flanged end wall, said cylindrical shield is slidably disposed in said annular space projecting through the bottom thereof, said cylindrical shield is formed with an upper radially outwardly directed flange, said first biasing means constitutes a compression spring disposed in said annular space and engaging said flange and said flanged end wall, said electric switch means includes a switch member, a leaf spring suspends said switch member inside said annular space, said switch member is formed with an inwardly directed lower hook below said flange of said cylindrical shield, said flange forming an extended paw above said lower hook and adapted to engage the latter when said cylindrical shield is moved downwardly a sufficient distance, an operating handle secured to a lower portion of said cylindrical shield, whereby the latter can be downwardly moved.

5. The densitometer according to claim 4, further comprising a light receiving assembly housing secured to said outermost vertically extending cylinder, a photomultiplier disposed in said light receiving assembly housing and communicating with the measuring light path, the latter passing through said innermost guide cylinder, said electric switch means includes a phototransistor operatively communicating with said photomultiplier and a shutter blade movably disposed between said photomultiplier, said shutter blade is connected to said switch member whereby the latter when moved by sufficient lowering of said cylindrical shield moves said shutter blade out from between said phototransistor and said photomultiplier enabling said electric switch means to detect light.

6. The densitometer according to claim 5, wherein said electric switch means includes a switching transistor biased by said phototransistor, a relay coil means operatively connected to said switching transistor and to said illumination lamp for turning off the latter in response to actuation of said switching transistor.

7. The densitometer according to claim 4, further comprising a hollow chip head secured inside said cylindrical shield at the bottom end thereof and constituting a part of said ambient light shielding cylinder, said hollow chip head has a lower circular wall defining a central opening, said hollow member is slidably disposed in said hollow chip head and has a central tubular portion projecting through said central opening defining a diffuser aperture, said hollow member includes an outwardly directed annular flange pointing to said hollow chip head, an annular washer held between said cylindrical shield and an upper end of said hollow chip head, said second biasing means constitutes a compression spring engaging said washer and said annular flange of said hollow member.

8. The densitometer according to claim 1, wherein said internal light shielding box comprises, an outer cylindrical wall having a lower end and an upper end and engagingly surrounding at said upper end said illumination plate, an opaque tube having a tube upper end passing centrally through said illumination plate, said tube upper end is formed with an aperture through which said measuring light path passes, and an opaque disc means for supporting said illumination lamp and having a central opening communicating with said opaque tube, said disc means is removably mounted in said lower end of said cylindrical wall.

9. The densitometer according to claim 1, wherein an opaque tube passes centrally through said illumination plate and extends up to an upper surface of the latter and said tube defines a circular first aperture adjacent said upper surface, a central aperture means formed at a bottom of the vertically movable ambient light shielding cylinder, the measuring light path passes through said first aperture and said aperture means, said central aperture means is formed with a diameter larger than that of said first aperture.

10. The densitometer according to claim 1, further comprising a measuring desk housing said illumination lamp and said light shielding box and defining a table formed with a stepped window opening, a main lamp means disposed in said measuring desk housing for providing the illumination light to the measuring light path and for providing internal illumination light for the sample stage, an annular diffusion plate disposed in said stepped window opening, annularly surrounding an upper end of said light shielding box and said annular illumination plate, and receiving internal illumination light from said main lamp means.

11. The densitometer according to claim 10, wherein said light shielding box is formed with a radially stepped upper edge complementarily engaging said annular diffusion plate.

* * * * *